United States Patent [19]

Riva

[11] 4,142,796
[45] Mar. 6, 1979

[54] BLOOD FLOW MEASUREMENT

[75] Inventor: Charles E. Riva, Acton, Mass.

[73] Assignee: Eye Research Institute of Retina Foundation, Inc., Boston, Mass.

[21] Appl. No.: 789,206

[22] Filed: Apr. 20, 1977

[51] Int. Cl.$^2$ ............................................. G01P 3/36
[52] U.S. Cl. ................................... 356/28; 128/2 T; 128/2.05 F
[58] Field of Search ................ 356/28, 39; 351/16; 128/2 T, 2.05 F; 73/194 E; 340/606

[56] References Cited

U.S. PATENT DOCUMENTS

| | | | |
|---|---|---|---|
| 3,373,441 | 3/1968 | Zadig | 356/28 |
| 3,390,577 | 7/1968 | Phelps et al. | 73/194 E |
| 3,417,754 | 12/1968 | Smart | 351/16 |
| 3,511,227 | 5/1970 | Johnson | 356/39 |
| 4,019,038 | 4/1977 | Critten et al. | 73/194 E |

OTHER PUBLICATIONS

Tanaka et al.; Science; vol. 186; Nov. 1974; pp. 830, 831.
Stern; Nature; vol. 254; Mar. 1975; pp. 56–58.

*Primary Examiner*—S. C. Buczinski
*Attorney, Agent, or Firm*—Wolf, Greenfield & Sacks

[57] ABSTRACT

A beam of laser light is impinged on a vessel or vessels in which blood is flowing, such as vessels in the retina of the eye. The reflected light is detected with a photodetector to product a signal representative of the Doppler shift frequencies of the light scattered from the moving blood cells. If the light is impinged on a capillary bed the photodetector produces a homodyne type signal, from light reflected from blood in the various capillaries; if the light is impinged on a single vessel the photodetector produces a heterodyne type signal from the light reflected from the vessel wall and the light reflected from the blood cells flowing in the vessel. The signal from the photodetector is amplified and used to drive an audio output to produce a sound representative of the velocity of the blood. Preferably the spot at which the blood flow is measured is observed by means of an ophthalmoscope to correlate the sound with a particular vessel or area of a capillary bed, and thereby to detect or arrive at a diagnosis of disease in the eye.

21 Claims, 3 Drawing Figures

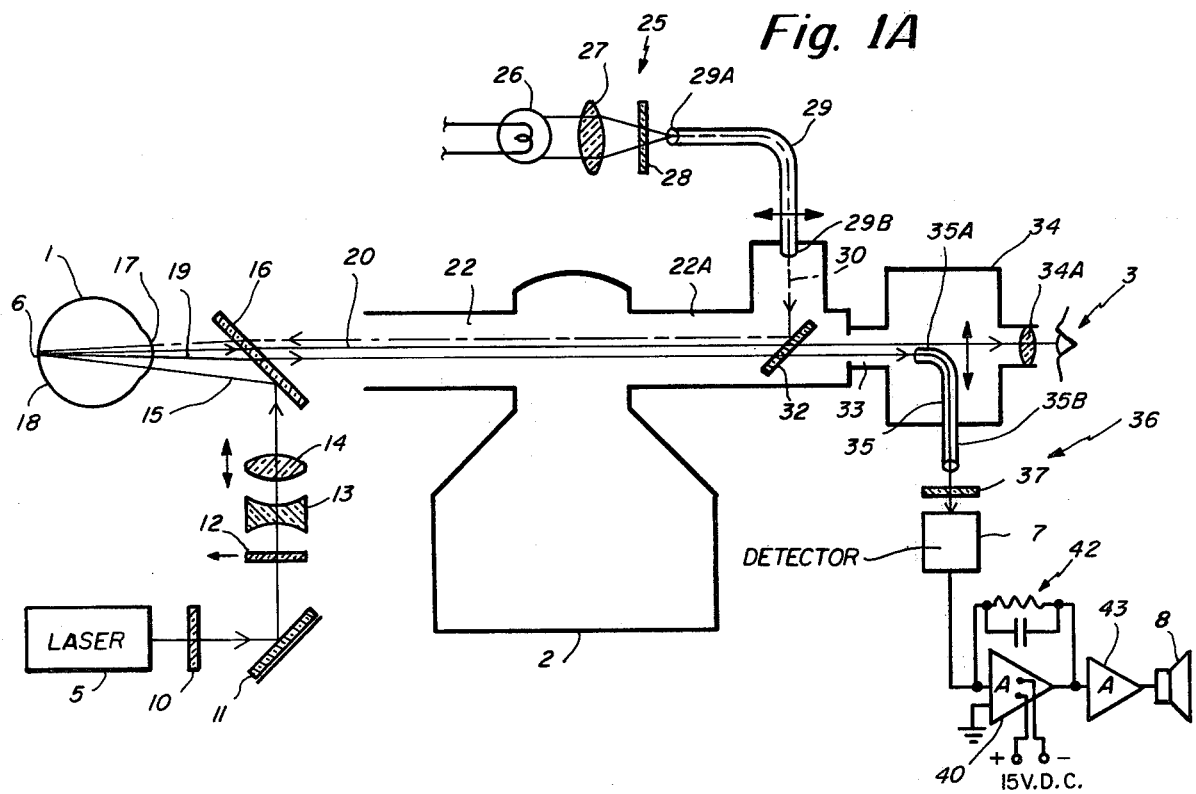
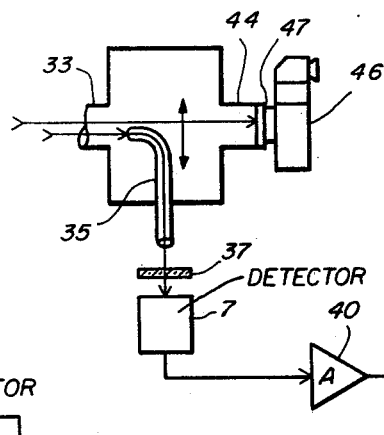
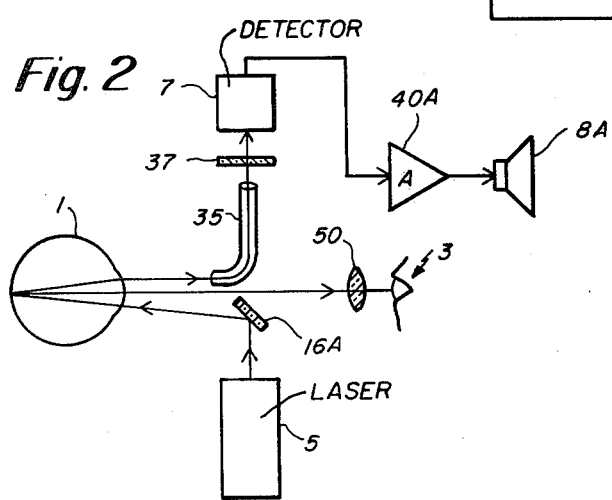

BLOOD FLOW MEASUREMENT

BACKGROUND OF THE INVENTION

The invention in general relates to methods and apparatus for detecting the velocity of blood flowing in a vessel. More particularly the invention relates to methods and apparatus for producing an audio signal representative of the velocity of blood in order to provide an instrument that can be used to routinely measure the velocity of blood flow in vessels, such as in the retina of the eye, and which can be used by any medical person.

The ability to measure the velocity of blood flowing in a single blood vessel or in a capillary bed is very useful for medical purposes. The restriction of blood circulation in various parts of the body has long been associated with disease and degeneration of both particular organs and the body as a whole. In particular it has become an accepted fact that impairment of blood flow in the tissues of the ocular fundus, or the retina of the eye, is associated with a large number of diseases that can lead to grave visual disorders. Blood flow measurements have also been used in the case of massive wounds to differentiate between tissues which have been killed, and which therefore must be removed to prevent gangrene, and tissues which are still living, and thus should not be removed.

Up to now information on blood flow in the body has been obtained by injecting dyes into the circulatory system and measuring the speed of the spread of the coloration. For example, retinal blood flow has been measured by fluorescein high speed cinematography. In this technique, fluorescein dye is injected into the circulatory system and the passage of the dye bolus in the fundus of the eye is recorded with a movie camera. The velocity of the blood is determined by measuring the distance traveled by the dye profile between successive frames of the film. This method is not adequate for routine clinical work, however, because it requires manipulating a catheter into the carotid artery. The information developed is also not immediately available because the film must be developed, and this usually requires a wait of at least several days before the film is returned from the film processing laboratory.

Recently a new technique for measuring the blood velocity in the retina of the eye has been demonstrated by this inventor. (See for example, Laser Doppler Measurement of Blood Flow In The Fundus Of The Human Eye, by C. E. Riva and G. T. Feke in Proceedings of the 1976 Electro-Optical Systems Design/International Laser Conference, pp. 142–147). This technique makes use of laser Doppler velocimetry (LDV). In LDV laser light is scattered from moving particles and the well-known Doppler effect leads to a frequency shift f between the frequency of the light scattered from the moving particle and the incident light frequency. The frequency shift f is related to the velocity V, the light wavelength $\lambda$ (in vacuo), and the scattering angle $\theta$ by the formula:

$$f = V/\lambda \sin \theta$$

In the new technique light is impinged on blood flowing in a blood vessel and the reflected light is detected by a photodetector. The light impinged on the vessel wall may be specularly reflected; however the term "reflected" when referring to the blood cells means non-specularly reflected, or scattered. The non-specularly reflected light is Doppler frequency shifted. The frequency shift given by the above formula then appears explicitly in the photocurrent output of the detector as a result of the inherent optical mixing process on the photocathode. Since normally in a blood vessel the blood cells flow at velocities varying over a range of velocities the photodetector output is a Doppler shift frequency spectrum (DSFS) which contains a range of frequency shifts corresponding to the range of particle velocities. In the technique demonstrated the frequency spectrum is plotted on a chart recorder as a function of the number of red blood cells which give rise to the Doppler shift of frequency f. The chart is then interpreted to give the blood velocity profile in the blood vessel and to diagnose any disorders associated with the indicated blood flow, or lack of blood flow.

The above described technique can be used to measure the blood flow in either an isolated vessel, or in a capillary bed. When the measurement is made on an isolated vessel light is reflected both from the wall of the vessel and from the red blood cells flowing in the vessel. Since the vessel wall is not moving the light reflected from it is not shifted in frequency. This light of unshifted frequency reflected from the wall of the vessel is incident on the photodetector along with the light of shifted frequency from the moving blood cells. The light of unshifted frequency acts as a reference beam the frequency of which is substracted out from each of the shifted frequencies by the optical mixing process in the photodetector, so that the output of the photodetector gives the frequency shifts directly. This type of optical mixing is called heterodyne mixing.

If the blood velocity is being measured in a capillary bed the reflectance from the tiny capillary walls is not sufficient to give heterodyne mixing. Thus the photodetector substracts one shifted frequency from another to give an output equivalent to a convolution of the heterodyne spectrum with itself. The resulting spectrum, called a homodyne spectrum, still contains all the information necessary to obtain the spectrum of blood velocities and thus can also be used as a diagnostic tool. The blood velocities in the capillary bed of the optic nerve in the retina of the eye are particularly important in diagnosing glaucoma.

Measurements of DSFS from red blood cells moving in tissues other than those in the eye have also been made. See for example M. D. Stern, "In Vivo Evaluation Of Microcirculation By Coherent Light Scattering", Nature, 1975, p. 56, Vol. 254.

The above described LDV techniques for measuring blood velocity have many advantages over the dye techniques. They are non-invasive and thus there is less chance that the measurement itself will affect the circulation system being measured. The laser intensities used are well below the intensities which might damage the tissue being preserved. In addition, use of a catheter, which requires highly trained experts, is not required. However the output of the above described systems is still in a form that is difficult to use in routine office or hospital tests because it requires bulky equipment and substantial skill and analysis.

SUMMARY OF THE INVENTION

It is an important object of this invention to provide means and methods for obtaining an indication of blood velocity in the form of an audible signal.

Another important object of the invention is to provide methods and apparatus for measuring blood velocity that can be used routinely in medical examinations by persons having ordinary training in use of common medical instruments.

The invention provides an LDV technique for measuring blood velocity having as an output a sound representative of the blood velocity in the vessel or vessels being examined, which sound can be recognized after a minimal amount of experience, as that corresponding to varying degrees of blood velocity which may represent healthy or unhealthy tissues.

The invention provides for impinging a beam of laser light on at least one vessel in which blood is flowing, and then detecting the light reflected with a photodetector. The photodetector output provides a signal representative of the Doppler shift frequencies of the light scattered from the moving blood cells. When blood flowing in a single vessel is being observed the photodetector output is a heterodyne signal; when the blood being observed is flowing in a capillary bed the photodetector output is a homodyne signal. The output signal from the photodetector is used to produce an audio output representative of the velocity of the blood. Preferably the photodetector signal is amplified and then used to drive an audio transducer, such as a speaker, to provide an audible sound representative of the velocity of the blood. The audio output may be recorded. The spot at which the laser beam impinges on the retina or other tissue may be observed, for example by means of an ophthalmoscope, in order to correlate the sound with the particular vessel or area of a capillary bed in which the blood flow is being measured, and thereby to detect or arrive at a diagnosis of disease or other disorder in the tissue being observed.

Numerous other features, objects and advantages of the invention will now become apparent from the following detailed description when read in conjunction with the accompanying drawing, in which:

BRIEF DESCRIPTION OF THE DRAWINGS

FIG. 1A is a diagrammatic illustration of a system according to the invention for detecting the velocity of blood flowing in a vessel in the retina of a human eye, and employing a fundus camera for observation of the area of the retina where the blood flow is being measured;

FIG. 1B is a partial view of a variation of the embodiment of the invention shown in FIG. 1, which variation includes a camera for photographing the area of the eye in which blood velocity is being detected and a tape recorder for recording the output of the photodetector;

FIG. 2 is an illustration of a system according to the invention for detecting the velocity of the blood in the retina of the human eye and employing an ophthalmoscope for observing the area of the retina in which the blood velocity is being detected.

DESCRIPTION OF THE PREFERRED EMBODIMENT

Directing attention to the drawing, FIG. 1A shows a system according to the invention for measuring the velocity of the blood flowing in vessels in the retina of a human eye 1, and employing a fundus camera 2 for observing at 3 the area 6 in the retina in which the blood velocity is being measured. Light produced by laser 5 is impinged on the retina of a human eye at 6. The light reflected is detected by photodetector 7 to produce a signal representative of the Doppler shift frequencies of the light scattered from the moving blood cells. The signal from detector 7 is used to produce at speaker 8 an audio output representative of the velocity of the blood.

Proceeding now with the detailed description of the various parts which make up the invention, light from laser 5 passes through density filter 10 which reduces the power of the laser light to a level low enough so that it will not damage the tissues of the eye, as for example 0.05 watts/cm$^2$ or less. Mirror 11 then directs the laser beam through a means for adjusting the beam diameter. A second density filter 12 is positioned during the adjusting process but is removed during the actual measurement. This second filter is a comfort and convenience factor for the patient and may be eliminated in some embodiments. The light then passes through lens system 13 and 14. Convex lens 14 can be moved in either direction along the optical path in order to adjust the beam diameter. First semi-transparent mirror 16 then directs the adjusted laser beam 15 through pupil 17 and onto retina 18 of eye 1. The locating of eye 1 so that beam 15 will be properly incident on the retina 18 and so that reflected beam 19 will be properly incident on the detecting means, shown generally at 36, and so that the spot 6 at which the beam is incident on the retina will be observable at 3, is determined by the fixating process described below.

The means for fixating is shown generally at 25. Light from a light source 26 is focused by lens 27, passes through colored filter 28, and is incident on one end 29A of optical fiber 29. The light passes through optical fiber 29, exits at the other end 29B, and is incident on a second semi-transparent mirror 32. Mirror 32 is positioned in relation to mirror 16 and end 35A of optical fiber 35 so that when eye 1 is fixated on the image of fiber end 29B in mirror 32 then beam 15 will be reflected from the retina along path 19 and will be incident on end 35A of optical fiber 35. Mirror 32, end 35A of optical fiber 35, and mirror 16 are positioned in relation to fundus camera 2, so that reflected beam 19 will travel substantially along the axis of fundus camera arm 22, thus making the spot 6 from which it originates viewable at 3, by adjusting lens 34A of the scanning ocular 34 in which fiber 35 is mounted.

The light reflected from the retina and incident on end 35A of fiber 35 then passes through the fiber, exits at end 35B, passes through colored filter 37 and is incident on photodetector 7 where it produces a signal representative of the velocity of the blood flowing at point 6. This output signal from photodetector 7 is amplified by pre-amplifier 40. The output signal from pre-amplifier 40 drives a conventional amplifier 43 and speaker 8 to produce a sound representative of a velocity of the blood flowing in the vessel or vessels at spot 6 of retina 18. RC loop 42 reduces high frequency noise.

The invention is operated by first having a person whose eye is to be examined focus his or her vision on the image of fiber end 29B in mirror 32. This fixation operation is not necessary for the successful measurement of the blood flow, however it helps prevent unwanted eye movement during the measurement process, and it also provides a means for precisely determining the position of the eye. Thus the eye may be returned to its original position if it is accidentally moved during the measurement, or if it becomes necessary to repeat the measurement.

With the eye fixated in position and density filter 12 in position in the beam, the beam diameter on the retina 18 is adjusted to its desired diameter by moving lens 14. The proper diameter depends on the type and size of the blood system being examined. If a single blood vessel is being examined the appropriate size is approximately the diameter of the vessel. If the beam is larger than the diameter of the vessel the blood in the tissues in the background of the vessel will contribute to the signal, sometimes making the measurement erroneous. If the beam is too small only the flow in a portion of the vessel will be measured. Since flow in a blood vessel is essentially parabolic, going from essentially zero at the wall to a maximum at the center, measurement of a portion of the flow will give a widely varying result, not easily relatable to the average flow of the blood in the vessel, which is generally the quantity of interest in diagnosing disease. Since the blood vessels in the eye are generally less than 250 $\mu$m in diameter the beam diameter is adjustable over a range below this size. In the embodiment shown, by observing at 3 the spot 6 illuminated by the laser beam, the laser beam may be adjusted by moving lens 14 until it is exactly the size of the vessel to be examined.

If the spot 6 being examined is in a capillary bed, adjustment of size of the beam diameter is not useful because the light is scattered by the tissue over a relatively broad area. In this mode the size of the image of fiber end 35A on the retina at spot 6 determines the size of the area examined. It has been found that a fiber having an end diameter of 450$\mu$m, which produces an image diameter of 250$\mu$m on the retina gives good results.

The position of end 35A of optical fiber 35 may be adjusted by a screw mechanism (not shown) so that it falls precisely in the center of the reflected beam. Density filter 12 is then removed and a measurement may be made. Before, during, or after a measurement, the spot 6 at which the blood velocity is being measured, may be observed at position 3 by means of lens 34A of scanning ocular 34 and the conventional optics of fundus camera 2. Briefly these consist of a light source for illuminating the retina and optics for producing a viewable or photographable image of the fundus or retina at the end of arm 22A. After one measurement is made the position of fiber end 29B may be altered slightly by means of a screw mechanism (not shown). If the eye is again fixated on the image of fiber end 29B in mirror 32 a different portion of retina 18 will be at spot 6, and thus the blood velocity at a different area may be measured. Alternatively, the blood velocity at different areas may be measured by adjusting mirror 16 and/or the position of end 35A of optical fiber 35.

The laser used in the embodiment shown is a HeNe laser. However, an argon laser or any other laser that has a wavelength that produces a frequency f in the audible range for common velocities of blood flow (about 2 centimeters per second) may be used. The frequency equation previously given can be used in selecting the laser wavelength. The HeNe laser is relatively inexpensive and produces red light which is very much scattered by red blood cells so that the intensity level of the light may be minimized. In the embodiment shown, light source 26 is a bulb and filter 28 is green. These could be replaced with an inherently green source such as an argon laser. A green filter is also used with the light source of the fundus camera 2. Filter 37 is red, and is preferably a gelatine Wratten filter; however any other filter that does not transmit light up to about 6000 angstroms (A) is suitable when using the HeNe laser. Filter 37 prevents the green light from the fixation light source 26 and the fundus camera light source from reaching the photodetector 7, but transmits the red laser light which carries the blood velocity information. If a laser other than a red laser is used, then other colors for the filters 28 and 37 and the fundus camera light source would be chosen that would eliminate the fixation and observation light but transmit the measurement light.

Semi-transparent mirror 16 is preferably about 0.125 mm in thickness and reflects about 4% of the incident laser light into the eye. Optical fiber 35 is preferably mounted in a scanning ocular, is movable in one direction, and has an aperture of 450$\mu$m. However, it is possible to use many other varieties and sizes of optical fibers. The ocular used is model 700-10-63 produced by Gamma Scientific of 3777 Ruffin Road, San Diego, California 92123. In the embodiment shown the optical fiber 29 has an aperture of approximately 200$\mu$m, however larger or smaller apertures are possible, the larger aperture providing less positive fixation and the smaller aperture being more difficult to see in mirror 32.

In the embodiment shown, photodetector 7 is an RCA photomultiplier model No. 8645 manufactured by RCA at 150 A Street, Needham Heights, Massachusetts 02194, and has an S-20 type spectral response. Other spectral response types such as S1, S10, etc. may be used, and in fact almost any photomultiplier may be used so long as it is sensitive to the red light of the HeNe laser. If a laser of another type is used the photomultiplier would be chosen to be sensitive to the light of that laser. In the embodiment shown the pre-amplifier 40 is a current-voltage converter, Model No. 3522L produced by Burr and Brown of P.O. Box 11400, Tucson, Arizona 85734. However with the photomultiplier used any pre-amplifier having a frequency response greater than 50 KHZ, an input impedance of about $10^{12}$ ohms and a bias current of about 1pA would be suitable. The use of other photomultipliers would require other suitable pre-amplifiers. The output of pre-amplifier 40 may be fed into almost any conventional amplifier and loudspeaker system.

FIG. 1B shows a variation of the embodiment of the invention shown in FIG. 1A in which a camera 46 replaces the eye of the observer 3 and a tape recorder 48 replaces amplifier 43 and speaker 8. The conventional fundus camera 2 is constructed so that a camera, such as a conventional 35 millimeter camera, can be mounted at the end of arm 22A in approximately the position of connector 33. It is clear therefore that a camera 46 can also be mounted at the end of arm 44 in order to photograph the spot on the fundus which is being measured. The only adjustment that is necessary, due to the slightly different position of mounting of the camera, is that the internal fundus camera focusing (not shown) or the lens 47 of camera 46 must be focused at a slightly longer distance. Almost any conventional tape recorder may be used to receive and record the signal from pre-amplifier 40. Except for these minor changes, the variation shown in FIG. 1B is identical to the embodiment discussed above in relation to FIG. 1A.

The fundus camera used in the above embodiments is one manufactured by Carl Zeiss Co., 444 Fifth Ave., New York, New York; however any fundus camera would be equally suitable.

FIG. 2 shows an embodiment of the invention in which a conventional ophthalmoscope replaces the fundus camera as the means for observing the spot on the retina at which the blood velocity measurement is being made. In this embodiment laser 5, optical fiber 35, filter 37, and photomultiplier 7 are identical to those used in the embodiments discussed above. The lens system used in the previous embodiments to adjust the beam diameter may also be used in this embodiment, or alternatively the mirror 16A may reflect less light than the mirror used in the previous embodiment and the size of the area examined may be determined by the aperture diameter of optical fiber 35. The observing means in this embodiment is any conventional ophthalmoscope, which is not shown in its entirety in FIG. 2 but is represented by its viewing lens 50. Briefly such a conventional ophthalmoscope consists of a light source for illuminating the interior of the eye, and a Rekoss wheel of lenses which permits the viewing of the interior of the eye at different magnifications. Lens 50 represents one of the lenses in such a Rekoss wheel. Amplifier 40A and speaker 8A are similar to the amplifiers and speaker used in the previous embodiments except that they are miniaturized.

The elimination of the fixating means in this embodiment and the replacement of the fundus camera observing means with the ophthalmoscope observing means (the latter which is conventionally a hand-sized instrument), permits the entire structure of the system of FIG. 2 to be reduced to a size that can be encased in the ophthalmoscope housing which can be held in one hand by the examiner. The focus point of the ophthalmoscope on the retina of the eye is chosen to coincide with the beam of the laser. Thus the invention may be aimed into the eye in the same manner as the conventional ophthalmoscope. Since a typical measurement time for a blood velocity measurement is currently about ½ to 1 second, eye stability is not a serious problem. Furthermore, as with the conventional ophthalmoscope, the medical examiner can be observing continually and thus can mentally note the area of the retina where an abnormal blood flow velocity is indicated.

In the embodiment shown in FIG. 1A the invention has been used to examine both healthy and unhealthy eyes. The sound produced by healthy tissue with high blood flow is a relatively high pitched sound. The sound produced by unhealthy tissue having low blood flow is a relatively low pitched sound. The sounds are easily distinguishable and in fact even an inexperienced person can readily recognize the sounds produced as that of liquid flow of varying velocities.

There has been described a novel method and apparatus that provides for the routine measurement of the velocity of blood flow in vessels in tissue such as the human eye, by persons having ordinary medical training. While the eye has been described here, the apparatus can be used to obtain sound output from blood vessels of the skin or other tissue. It is evident that those skilled in the art may now make numerous uses and modifications of and departures from the specific embodiments described herein without departing from the inventive concepts. Many variations of the optical path of the laser light may be employed, the only requirement being that a laser and a photodetector be employed with the light being reflected from the moving blood cells between the two instruments. The audio output may also take on a wide variety of forms, in fact almost any of the forms available in the extensive audio amplification and reproduction art may be used. Many different observing systems may also be used, or the observing operation may be eliminated entirely with the examiner making a judgment of healthiness or unhealthiness of the tissue from his experience in interpreting the output sound.

What is claimed is:

1. A method for measuring blood velocity comprising:
   (a) impinging a beam of laser light on at least one vessel in which blood is flowing,
   (b) detecting the light reflected with a photodetector to produce a signal representative of the Doppler shift frequencies of the light scattered from the moving blood cells,
   (c) producing from the signal an audio output representative of the velocity of the blood.

2. A method for measuring blood velocity in accordance with claim 1 wherein the step of producing comprises:
   amplifying the signal, and
   driving a transducer with the amplified signal to produce a sound representative of the velocity of the blood.

3. A method for measuring blood velocity in accordance with claim 1 and further including the step of recording the audio output.

4. A method for measuring blood velocity in accordance with claim 3 and further including the step of photographing the spot at which the laser beam impinges upon the vessel.

5. A method for measuring blood velocity in accordance with claim 2 wherein the step of impinging comprises impinging the light on vessels in a capillary bed.

6. A method for measuring blood velocity in accordance with claim 2 wherein:
   the step of impinging comprises impinging the light on a single vessel, and
   the step of detecting comprises detecting the light reflected from the vessel wall and the light scattered from the blood flowing in the vessel.

7. A method for measuring blood velocity in accordance with claim 6 and further comprising the step of observing the spot at which the beam impinges upon the vessel.

8. A method for measuring blood velocity in accordance with claim 7 wherein the step of impinging comprises impinging the beam of light on a vessel in the retina of the human eye.

9. A method for measuring blood velocity in accordance with claim 8 and further comprising the step of fixating the eye on a target while impinging the light on the vessel in the eye.

10. A method for measuring blood velocity in accordance with claim 9 and further comprising the step of adjusting the beam of light to less than about 250µm in diameter prior to impinging it on the vessel.

11. A method for measuring blood velocity in accordance with claim 9 and further comprising the step of adjusting the size of the laser beam spot and spot of observing to a size corresponding to the vessel size.

12. A method for measuring blood velocity in accordance with claim 5 wherein:
   the step of impinging includes impinging the light on a capillary bed in the retina of the human eye,
   and further comprising the steps of:
   fixating the eye on a target while impinging the light on the capillary bed, and
   observing the spot at which the beam impinges on the capillary bed.

13. A device for measuring blood velocity comprising:
   (a) a laser for producing a beam of light, (b) a means for impinging the beam of light on at least one vessel in which blood is flowing,
(c) a means for detecting the light reflected to provide a signal representative of the Doppler shift frequencies of the light,
(d) a means for producing from the signal an audio output representative of the velocity of the blood.

14. A device for measuring blood velocity in accordance with claim 13 wherein the means for impinging comprises a means for impinging the beam on at least one vessel in the retina of the human eye and further comprising:
   means for fixating the eye,
   means for adjusting the size of the beam spot to a size corresponding to the size of the vessel in which the blood velocity is to be measured,
   means for observing the spot at which the beam impinges.

15. A device for measuring blood velocity in accordance with claim 13 wherein the means for producing comprises:
   an amplifier for amplifying the signal, and
   transducer means for receiving the amplified signal and providing a sound representative of the blood velocity.

16. A device for measuring blood velocity in accordance with claim 14 wherein:
   the means for impinging comprises:
   a first semi-transparent mirror positioned in the beam whereby the beam is reflected through the pupil of the eye and onto the vessel,
   the means for fixating comprises:
   a target light source,
   a second semi-transparent mirror,
   a first optical fiber, one end of which intercepts light from the target source, and the other end of which is positioned so that the exiting light is incident on the second mirror,
   said second mirror being positioned so that when the eye is fixated on the image of the fiber end in the mirror, the laser light reflected from the retina is incident on the means for detecting,
   the means for detecting comprises:
   a photodetector, and
   a second optical fiber, having one end positioned along the path of the reflected light and the other end positioned so that light exiting from it is incident on the photodetector,
   the means for adjusting comprises a lens system positioned in the beam between the laser and the first mirror, and
   the means for producing comprises:
   an amplifier for amplifying the signal, and
   transducing means for receiving the amplified signal and providing a sound representative of the velocity of the blood.

17. A device for measuring blood velocity in accordance with claim 16 wherein said means for observing comprises a fundus camera.

18. A device for measuring blood velocity in accordance with claim 16 wherein:
   the laser is a red HeNe laser,
   the target light source is a source of green light,
   the means for observing includes a green light source,
   and further comprising a red filter placed between the end of the first optical fiber and the photodetector thereby preventing substantially all the green light from entering the photodetector but transmitting the red light.

19. A device for measuring blood velocity in accordance with claim 13 and further comprising an ophthalmoscope for observing the spot at which the beam impinges.

20. A device for measuring blood velocity in accordance with claim 13 and further comprising a means for recording the audio output.

21. A device for measuring blood velocity in accordance with claim 20 and further comprising a means for photographing the spot at which the laser beam impinges on the vessel.

* * * * *